United States Patent [19]

Hashimoto et al.

[11] Patent Number: 5,161,537
[45] Date of Patent: Nov. 10, 1992

[54] ULTRASONIC DIAGNOSTIC SYSTEM

[75] Inventors: Masahiko Hashimoto, Tokyo; Shinichiro Ueno, Sagamihara; Hiroshi Fukukita, Tokyo; Tsutomu Yano; Akihisa Adachi, both of Kawasaki, all of Japan

[73] Assignee: Matsushita Electric Industrial Co., Ltd., Osaka, Japan

[21] Appl. No.: 672,413

[22] Filed: Mar. 20, 1991

[30] Foreign Application Priority Data

Mar. 26, 1990 [JP] Japan ................................. 2-76041
Nov. 27, 1990 [JP] Japan ................................. 2-328688

[51] Int. Cl.⁵ .............................................. A61B 8/12
[52] U.S. Cl. ...................... 128/662.06; 128/661.01; 128/662.03
[58] Field of Search ................ 128/661.01, 662.05, 128/662.06, 660.03, 662.03, 4, 6

[56] References Cited

U.S. PATENT DOCUMENTS

| | | | |
|---|---|---|---|
| 4,895,158 | 1/1990 | Kawabuchi et al. | 128/662.06 |
| 4,945,767 | 8/1990 | Shirasaka | 128/661.01 |
| 4,991,588 | 2/1991 | Pflueger et al. | 128/662.06 |
| 5,022,399 | 6/1991 | Biegeleisen | 128/662.06 |
| 5,038,789 | 8/1991 | Frazin | 128/662.06 |
| 5,054,491 | 10/1991 | Saito et al. | 128/662.06 |
| 5,081,993 | 1/1992 | Kitney et al. | 128/662.06 |

OTHER PUBLICATIONS

"High Resolution Intravascular Imaging Via Ultrasonic Catheters: Proof of Concept"; by Charles R. Meyer et al; Proceedings of the IEEE, vol. 76, No. 9, Sep. 1988; pp. 1074–1077.

*Primary Examiner*—Kyle L. Howell
*Assistant Examiner*—George Manuel
*Attorney, Agent, or Firm*—Pollock, VandeSande & Priddy

[57] ABSTRACT

An ultrasonic probe has an elongated form with an end. A transducer element array is disposed in the probe for emitting ultrasonic wave frontward with respect to the end of the probe and receiving echo ultrasonic waves. The transducer element array converts the received echo ultrasonic waves into corresponding electric echo signals. The electric echo signals are processed according to a predetermined aperture synthesis technique, and thereby an image signal is generated on the basis of the electric echo signals. An image of a region in front of the end of the probe is reproduced in response to the image signal.

5 Claims, 12 Drawing Sheets

ULTRASONIC DIAGNOSTIC SYSTEM

BACKGROUND OF THE INVENTION

1. Field of the Invention

This invention relates to an ultrasonic diagnostic system having an ultrasonic probe which is inserted into an used in coeloms or tubes of a body to obtain sectional images of internal parts of the body.

2. Description of the Prior Art

Proceedings of the IEEE, pages 1074–1077, Vol 76, No 9, 1988, discloses a very-small catheter-type ultrasonic probe which is to be inserted into and used in coeloms or tubes of a body to obtain sectional images of internal parts of the body. The prior art ultrasonic probe of the IEEE documents has an elongated casing, and is designed to obtain sectional images of parts of the body which extend around the sides of the casing. It is difficult for the prior art ultrasonic probe of the IEEE documents to obtain sectional images of parts of the body which extend in front of an end of the casing.

U.S. Pat. No. 4,895,158 discloses an ultrasonic probe which is inserted into and used in coeloms of a body to obtain sectional images of internal parts of the body. The prior art ultrasonic probe of U.S. Pat. No. 4,895,158 has an elongated casing, and is designed to obtain sectional images of parts of the body which extend in front of an end of the casing. The prior art ultrasonic probe of U.S. Pat. No. 4,895,158 is of the mechanically scanning type. The mechanically scanning tends to cause a considerable obstacle to the miniaturization of the ultrasonic probe.

SUMMARY OF THE INVENTION

It is an object of this invention to provide an improved ultrasonic diagnostic system.

A first aspect of this invention provides an ultrasonic diagnostic system comprising an elongated probe having an end; a transducer element array disposed in the probe for emitting ultrasonic wave frontward with respect to the end of the probe and receiving echo ultrasonic waves, the transducer element array converting the received echo ultrasonic waves into corresponding electric echo signals; means for processing the electric echo signals according to a predetermined aperture synthesis technique, and for generating an image signal on the basis of the electric echo signals; and means for reproducing an image of a region in front of the end of the probe in response to the image signal.

A second aspect of this invention provides an ultrasonic diagnostic system comprising a catheter having an end; and a transducer element array disposed in the end of the catheter for emitting ultrasonic wave frontward with respect to the end of the catheter and receiving echo ultrasonic waves to scan a region in front of the end of the catheter.

A third aspect of this invention provides an ultrasonic diagnostic system comprising a catheter having an end; a transducer element array disposed in the end of the catheter for emitting ultrasonic wave frontward with respect to the end of the catheter and receiving echo ultrasonic waves to scan a region in front of the end of the catheter; and means for emitting a laser light beam frontward from the end of the catheter.

DESCRIPTION OF THE FIRST PREFERRED EMBODIMENT

Figure 1:
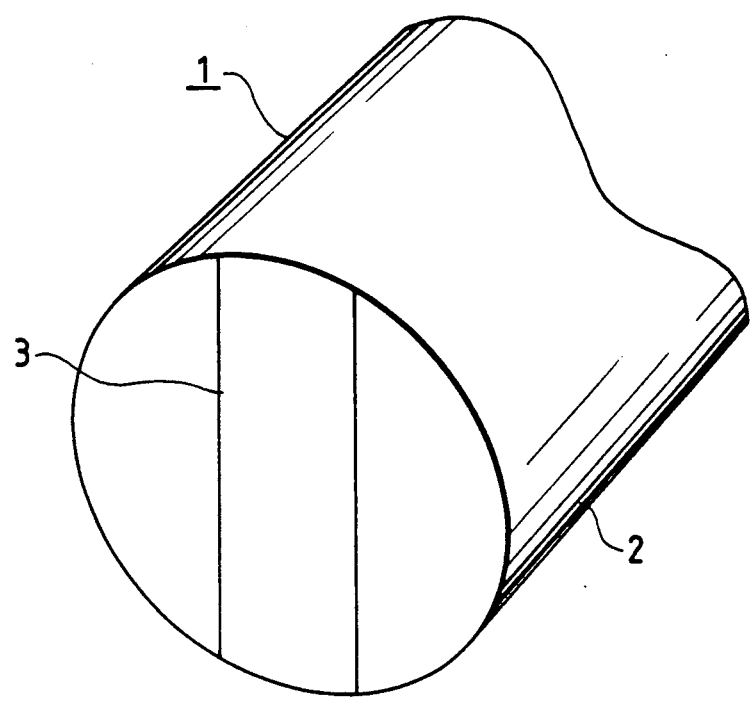
FIG. 1 is a perspective view of an ultrasonic probe in an ultrasonic diagnostic system according to a first embodiment of this invention.
Figure 2:
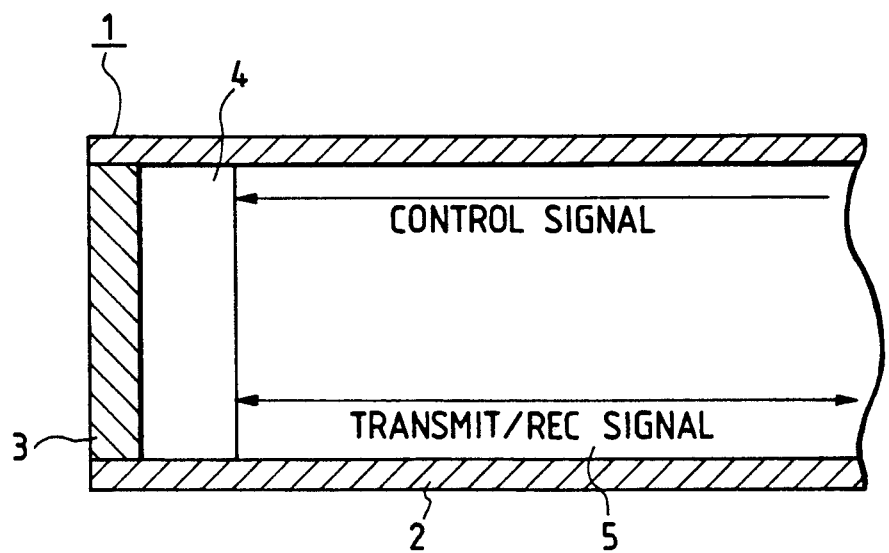
FIG. 2 is a sectional view of the ultrasonic probe of FIG. 1.

With reference to FIGS. 1 and 2, an ultrasonic diagnostic system includes an ultrasonic probe 1 having a cylindrical casing 2. An array 3 of ultrasonic-to-electrical transducer elements is disposed in a front end of the casing 2. The transducer element array 3 is provided with an acoustic lens, a matching layer, and a backing layer in a known manner. An electronic circuit 4 associated with the transducer element array 3 is accommodated in the region of the casing 2 which extends adjacently rearward of the transducer element array 3. A plurality of signal lines connected to the electronic circuit 4 extend in the interior 5 of the casing 2 to conduct a transmission signal, a received signal, and a control signal to and from the electronic circuit 4.

In the transducer element array 3, the transducer elements are aligned along a line. In other words, the transducer element array 3 has a linear arrangement. The transducer element array 3 has an active surface (a transmitting/receiving surface) via which ultrasonic waves are transmitted and received. The active surface of the transducer element array 3 faces frontward with respect to the casing 2. The electronic circuit 4 is of a known structure, having a channel-changing function and a transmission/reception (T/S) switching function. During the transmission and the reception of ultrasonic waves via the transducer element array 3, the electronic circuit 4 selects one or more of the transducer elements as active elements and sequentially changes the active elements in a known manner. The electronic circuit 4 is electrically connected to a main part of the ultrasonic diagnostic system via the signal lines.

Figure 3:
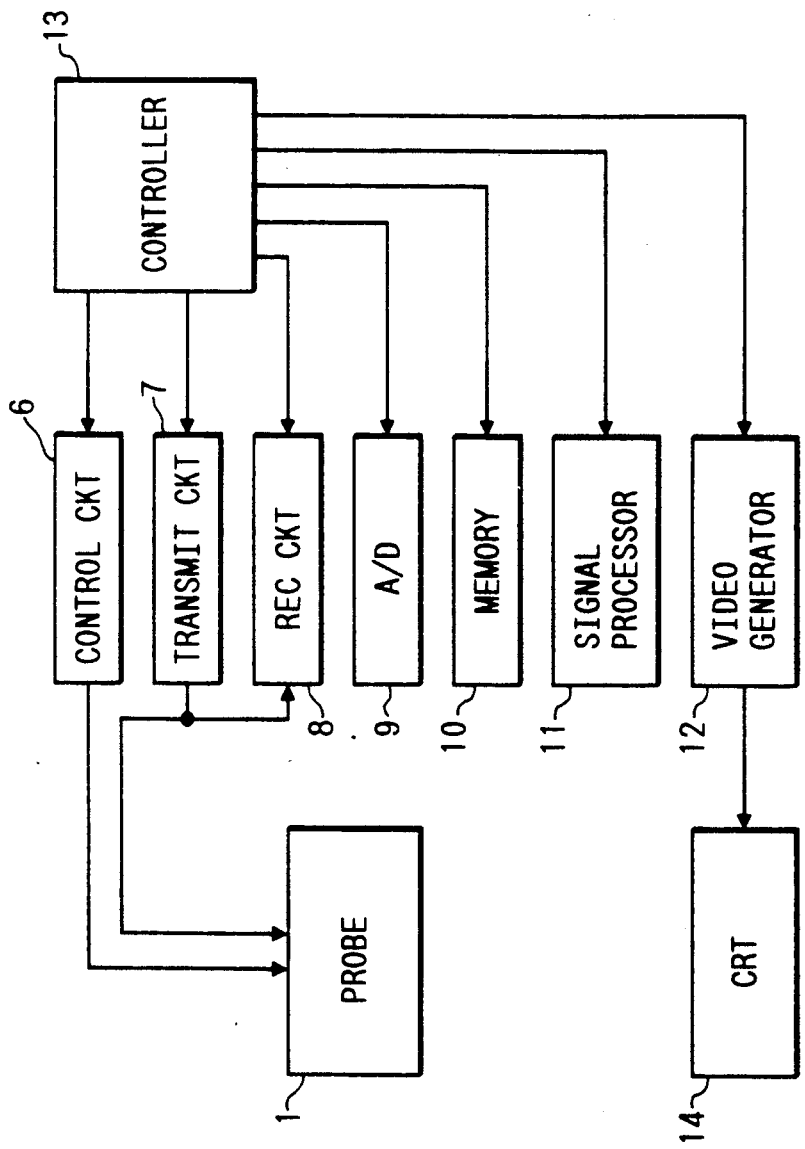
FIG. 3 is a block diagram of the ultrasonic diagnostic system according to the first embodiment of this invention.

As shown in FIG. 3, the main part of the ultrasonic diagnostic system includes a control circuit 6, a transmission circuit 7, and a reception circuit 8 connected to the electronic circuit 4 within the ultrasonic probe 1. The control circuit 6 serves to control the electronic circuit 4 in response to a signal fed from a controller 13. The transmission circuit 7 feeds a transmission signal to the transducer element array 3 via the electronic circuit 4 in response to a signal fed from the controller 13, and the transducer element array 3 emits ultrasonic wave in response to the transmission signal. Echoes of ultrasonic wave are received by the transducer element array 4 and are converted by the transducer element array 4 into corresponding electric echo signals, which are transmitted to the reception circuit 8 via the electronic circuit 4 and are amplified and processed by the reception circuit 8 in response to a signal fed from the controller 13.

The output signal from the reception circuit 8 is converted by an A/D converter 9 into a corresponding digital signal, which is stored into a memory 10. Timings of operation of the A/D converter 9 and the memory 10 are controlled by signals fed from the controller 13. The digital signal is read out from the memory 10, and is then processed by a signal processor 11 into image data in response to a signal fed from the controller 13. The image data is converted by a video generator 12 into a corresponding video signal in response to a signal fed from the controller 13. The video generator 12 includes a digital scan converter. The video signal is fed from the video generator 12 to a CRT 14, and an image represented by the video signal is indicated by the CRT 14. The devices 6–12 are controlled by the controller 13.

The ultrasonic diagnostic system of FIGS. 1–3 operates as follows. The ultrasonic probe 1 is inserted into a tube, a blood vessel, or a coelom of an examined body. One or more of the transducer elements in the transducer element array 3 are sequentially selected by the electronic circuit 4 as active transducer elements in response to a control signal fed from the control circuit 6. The selected transducer elements are fed with a transmission signal from the transmission circuit 7, emitting ultrasonic wave pulses toward a region of the body which extends in front of the end of the probe casing 2.

Portions of the emitted ultrasonic wave pulses are reflected within the body, being returned to the transducer element array 3 as echo pulses. The echo pulses received by the selected transducer elements (the active transducer elements) are converted into corresponding electric echo signals, which are transmitted to the reception circuit 8 via the electronic circuit 4.

The transducer elements in the transducer element array 3 compose a given number of different channels. During the transmission and the reception of the ultrasonic wave pulses, the selected transducer elements are changed to sequentially activate the channels to scan a given region of the body which extends in front of the probe casing 2.

The electric echo signals are amplified and processed by the reception circuit 8. The output signal from the reception circuit 8 is converted by the A/D converter 9 into a corresponding digital signal, which is stored into the memory 10. The previously-mentioned process is reiterated and thus the digital signal is accumulated in the memory 10 until the digital signal in the memory 10 corresponds to a desired complete image of the body.

The signal processor 11 reads out the digital signal from the memory 10, subjecting the digital signal to a delaying process, a weighting process, and an adding process in accordance with an aperture synthesis technique and thereby converting the digital signal into image data. The image data is converted by the video generator 12 into a corresponding video signal. The video signal is fed from the video generator 12 to the CRT 14, and the image represented by the video signal is indicated by the CRT 14. The indicated image agrees with a sectional image of the region of the body which extends in front of the end of the probe casing 2. A sequence of the previously-mentioned operations is controlled by the controller 13. For this purpose, the controller 13 includes a time base.

The outside diameter of the ultrasonic probe 1 is preferably set to a small value, for example, 2 mm or less so that the ultrasonic probe 1 can be used within a small tube or coelom of the body. Since the ultrasonic probe 1 scans the region of the body which extends in front of the end of the probe casing 2, a block of the tube or coelom of the body can be accurately observed.

Since the electronic circuit 4 is located adjacently rearward of the transducer element array 3, signal lines connected between the electronic circuit 4 and the transducer element array 3 are prevented from extending through a great part of the interior 5 of the probe casing 2. This is advantageous for the miniaturizatin of the ultrasonic probe 1. When the electronic circuit 4 is composed of an IC chip, the ultrasonic probe 1 can be further miniaturized.

The frequency of the used ultrasonic wave is preferably set to a value within a range of 20 MHz to 40 MHz in consideration of the damping of the ultrasonic wave, the resolution of the obtained image, and the sizes of the ultrasonic probe 1 and the examined coelom and tube of the body. The transducer elements are preferably made of high-molecule piezoelectric material such as PVDF.

DESCRIPTION OF THE SECOND PREFERRED EMBODIMENT

FIGS. 4–10 relate to an ultrasonic diagnostic system according to a second embodiment of this invention which is similar to the embodiment of FIGS. 1–3 except for design changes indicated hereinafter.

Figure 4:
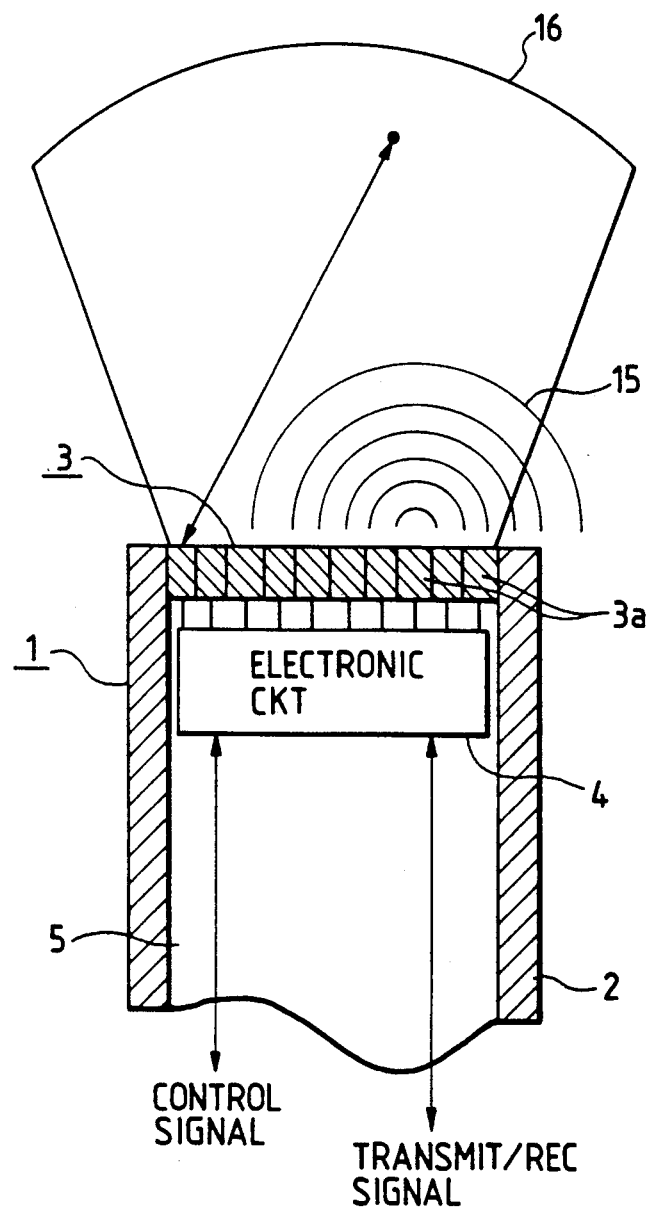
FIG. 4 is a sectional view of an ultrasonic probe in an ultrasonic diagnostic system according to a second embodiment of this invention.

In FIG. 4, the reference character 3a denotes transducer elements composing a transducer element array 3 disposed in a front end of a casing 2 of an ultrasonic probe 1. An electronic circuit 4 associated with the transducer element array 3 includes an analog multiplexer which enables a decrease in the number of required signal lines. The analog multiplexer 4 has a function of changing connections corresponding to respective channels. For the simplicity of transmission and reception control, the analog multiplexer 4 is designed so that ultrasonic wave will be transmitted and echo utltrasonic wave will be received by a same transducer element 3a which constitutes an active element. One of the transducer elements 3a in the transducer element array 3 is sequentially selected by the multiplexer 4 as an active element for scanning a given sector region 16 of an examined body which extends in front of the end of the probe casing 2.

Each transducer element 3a has a broad directivity 15 close to a non-directional characteristic. During a single transmission and reception process, an active transducer element 3a receives echo ultrasonic waves from a wide region of an examined body which extends in front of the end of the probe casing 2. The received echo ultrasonic waves are converted by the active transducer element 3a into a corresponding electric signal. The electric signal is fed to a main part of the ultrasonic diagnostic system via the analog multiplexer 4 and signal lines, being processed and converted into a corresponding digital signal as in the embodiment of FIGS. 1–3. The digital signal is stored into a memory 10 of FIG. 5. Specifically, time segments of the digital signal are sequentially stored into storage locations (storage segments) of the memory 10. It should be noted that the connection of the memory 10 to the analog multiplexer 4 is omitted from FIG. 5.

Figure 5:
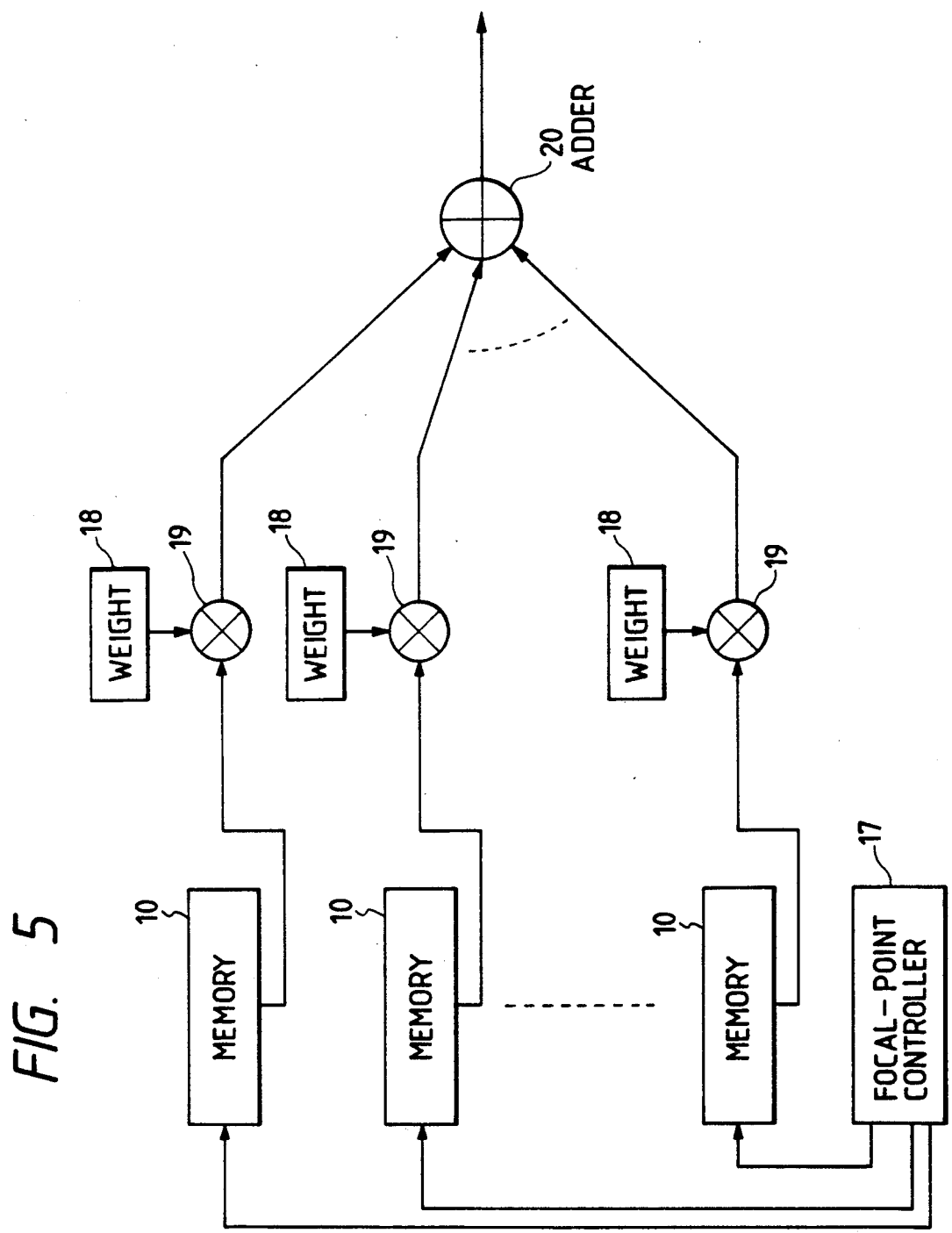
FIG. 5 is a block diagram of a signal processing part of the ultrasonic diagnostic system according to the second embodiment of this invention.

In FIG. 5, a focal-point controller 17 serves to control a segment of the memory 10 from which data is read out. Specifically, the focal-point controller 17 includes an address controller operating on the memory 10. Data read out from the segments of the memory 10 are fed to multipliers 19 respectively. The multiplier 19 multiplies the fed data by weights 18 respectively. The output data from the multipliers 19 which represent the results of the multiplications are added by an adder 20.

Since time segments of the echo digital signal correspond to different object points to be imaged and since the time segments of the echo digital signal are sequentially stored into storage locations (storage segments) of the memory 10, the addresses of the storage locations of the memory 10 have a fixed relation with the object points to be imaged. For each object point to be imaged, the focal-point controller 17 calculates a related address on the basis of the distance between the used transducer element 3a and the object point, and the focal-point controller 17 feeds the calculated address to the memory 10 so that data is read out from the segment to the memory 10 which is designated by the calculated address. The address fed to the memory 10 is periodically updated so that data will be sequentially read out from the segments of the memory 10. The data read out from the segments of the memory 10 are fed to the multipliers 19 respectively. Thus, the multipliers 19 correspond to the respective object points. The weights 18 fed to the multipliers 19 are preset so as to depend on the distances between the used transducer element 3a and the corresponding object points. The multipliers 19 multiply the data by the weights 18. The output data from the multipliers 19 are combined by the adder 20 into image data which sequentially represents images of the object points. The previously-mentioned signal processing is executed for each of object points within the sector scanned region 16 of the body, so that image data corresponding to an image of the scanned region 16 can be obtained finally.

Figure 6:
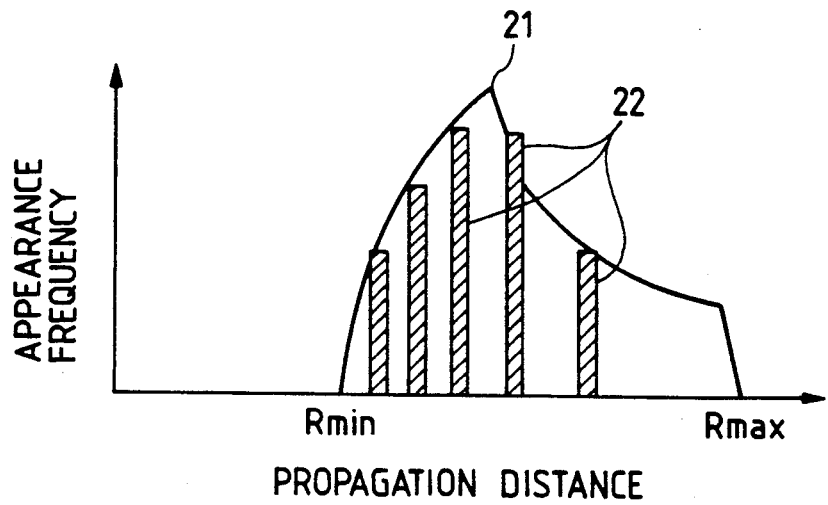
FIG. 6 is a diagram showing the relation between a propagation path distribution and a weighting function.

In FIG. 6, the numeral 21 denotes a distribution of propagation paths between the transducer elements 3a and the object points which occur in the case where the transducer elements 3a are continuously arranged. As shown in FIG. 6, a weighting function 22 which determines the weights 18 is set into agreement with the propagation path distribution 21. This design enables the suppression of components of the image data which are caused by a grating lobe of the transducer element array 3. It should be noted that the grating lobe results from an equally-spacing arrangement of the transducer elements 3a.

In the case of a linear arrangement of the transducer elements 3a, a propagation path distribution P(r) can be statistically expressed by the following equations.

$$P(r) = R/(R^2 - Y^2)^{1/8} \text{ when } Rmin \leq R \leq Rmax$$

$$P(r) = 0 \text{ when } R < Rmin, R > Rmax \tag{1}$$

where the character R denotes the distance between a transducer element and an object point; the characters Rmin and Rmax denote predetermined limits; and the character Y denotes the distance between the line of the transducer elements and the object point. A forward and backward propagation path distribution Ptr(r) is given as a convolution of the equations (1), and is expressed by the following equation.

$$Ptr(r) = P(R) * P(r) \tag{2}$$

The weighting function determining the weights 18 is chosen on the basis of the equations (1) and (2).

It should be noted that a propagation path distribution can be calculated for a convex configuration of transducer elements, and that a used propagation path distribution is required to depend on a configuration of transducer elements.

Figure 7:
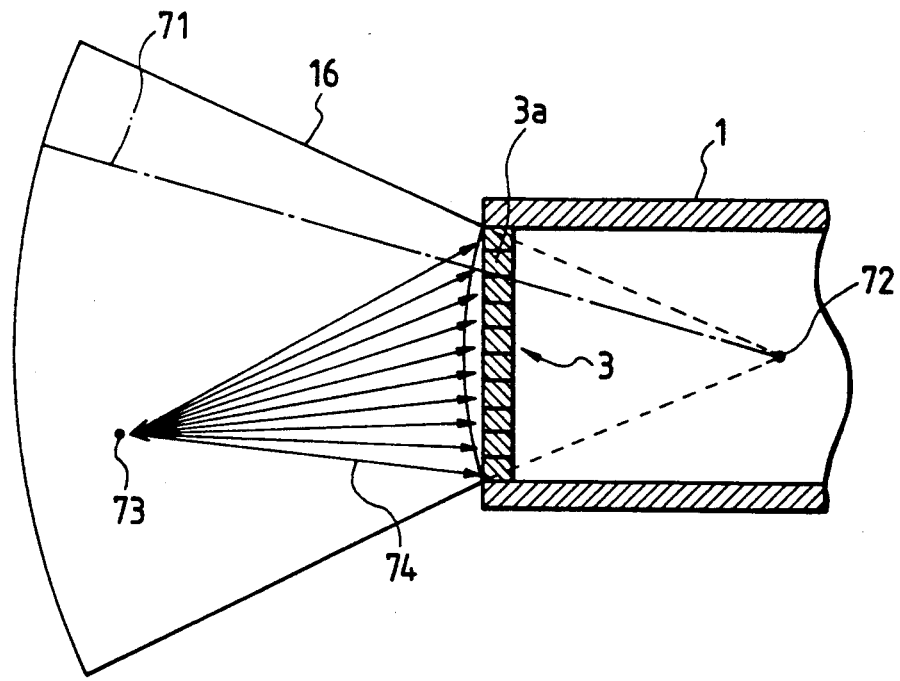
FIG. 7 is a sectional view of the ultrasonic probe in the ultrasonic diagnostic system according to the second embodiment of this invention.

As shown in FIG. 7, the sector scanned region 16 is truncated, and an imaginary vertex is defined as a reference point 72 with respect to the sector scanned region 16. Scanning lines 71 compose the sector scanned region 16. Extensions of the scanning lines 71 pass through the reference point 72. It is now assumed that a reflection point 73 at which ultrasonic waves emitted from the transducer elements 3a are reflected is present within the sector scanned region 16 as shown in FIG. 7. There are propagation paths 74 via which forward and backward ultrasonic waves travel between the transducer elements 3a and the reflection point 73. The reference point 72 is chosen to lie rearward of the transducer element array 3 so that a dead angle of the ultrasonic probe 1 can be decreased and a visual field of the ultrasonic probe 1 can be widened.

A further description will be given hereinafter with reference to FIG. 8. As described previously, a transmission and reception process is executed for each of the transducer elements 3a by the operation of the analog multiplexer 4. An electric echo signal corresponding to one transducer element 3a is transmitted from the traducer element 3a to a reception circuit 8 via the analog multiplexer 4, being amplified by the reception circuit 8 and then being converted by an A/D converter 9 into a corresponding digital echo signal. The memory 10 includes line segments which correspond to the transducer elements 3a respectively. The digital echo signal corresponding to one transducer element 3a is stored into the corresponding line segment of the memory 10. Since the analog multiplexer 4 sequentially selects one of the transducer elements 3a, the digital signals corresponding to the transducer elements 3a are stored into the corresponding line segments of the memory 10 respectively.

Figure 8:
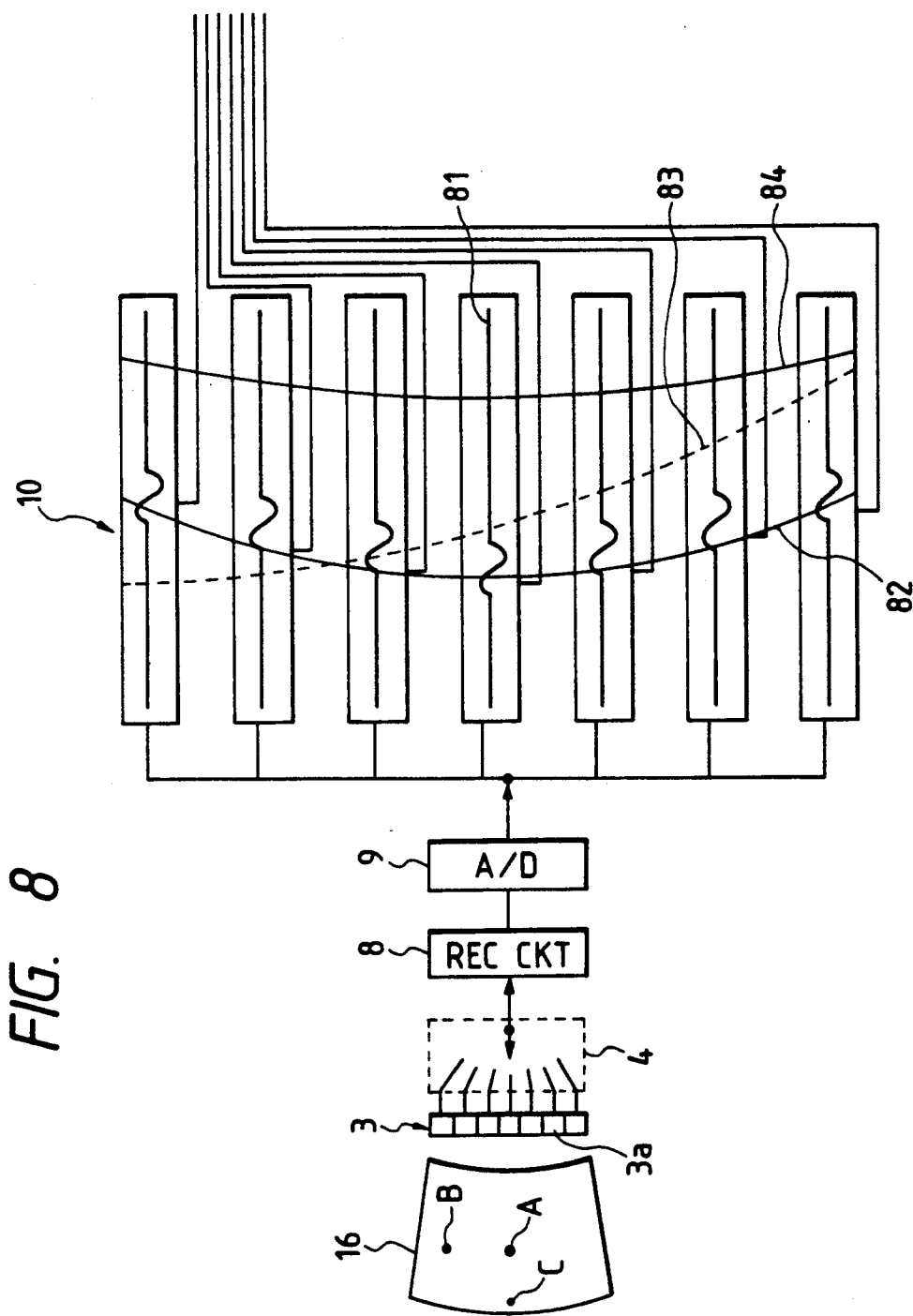
FIG. 8 is a block diagram of a signal changing part and a signal processing part of the ultrasonic diagnostic system according to the second embodiment of this invention.

A consideration will be given of three points A, B, and C which lie within the sector scanned region 16 as shown in FIG. 8. It is now assumed that the point A agrees with a reflection point. In this case, the digital signals stored in the line segments of the memory 10 represent respective waveforms 81 such as shown in FIG. 8. A signal representing conditions of the point A is synthesized on the basis of data read out from storage locations of the line segments of the memory 10 which are arranged along a curved line 82. A signal representing conditions of the point B is synthesized on the basis of data read out from storage locations of the line segments of the memory 10 which are arranged along a curved line 83. A signal representing conditions of the point C is synthesized on the basic of data read out from storage locations of the line segments of the memory 10 which are arranged along a curved line 84. Reading data from storage locations of the line segments of the memory 10 is executed in a sequence determined by a scanning line 71 of FIG. 7.

Figure 9:
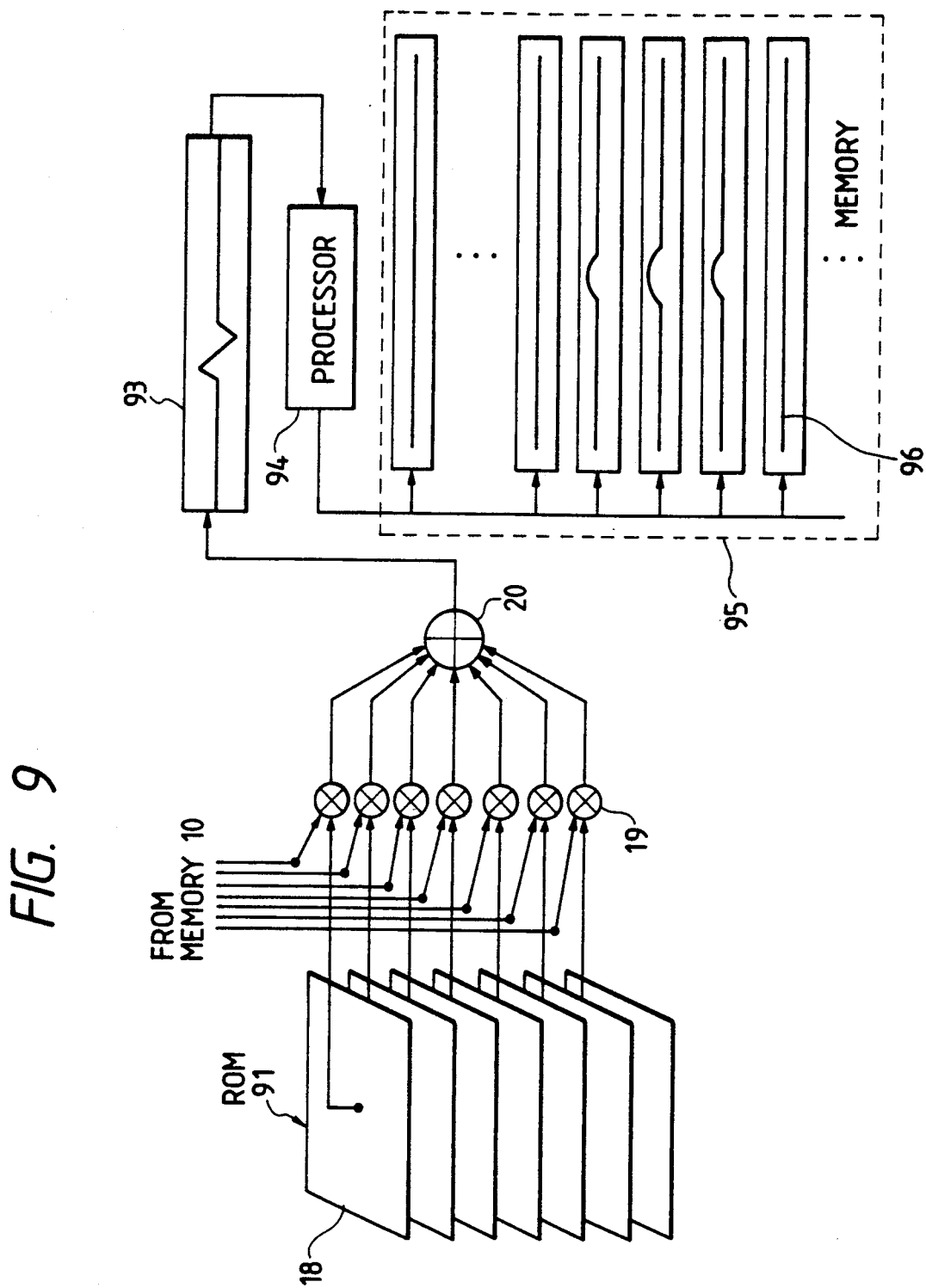
FIG. 9 is a block diagram of a signal processing part of the ultrasonic diagnostic system according to the second embodiment of this invention.

As shown in FIG. 9, the weights 18 are fed to the multipliers 19 respectively. The weights 18 are outputted from a ROM 91 which previously stores a map containing data of the weights 18. The multipliers 19 are fed with the data from the line segments of the memory 10 respectively, and multiply the data by the weights 19 respectively. As described previously, the weights 18 are designed in correspondence with the transducer elements 3a so as to suppress components of resultant image data which are caused by a grating lobe of the transducer element array 3. Further, the weights 18 are predetermined in correspondence with respective object points. The output data from the multipliers 19 are combined by the adder 20 into a time segment of a resultant signal 93 which corresponds to one object point on a scanning line 71. The weighting process by the multipliers 19 and the adding process by the adder 20 are periodically reiterated for all object points on a scanning line 71, so that the resultant signal 93 corresponding to a complete scanning line 71 is obtained finally. A processor 94 subjects the resultant signal 93 to compression and detection so that a desired dynamic range of a reproduced image can be satisfied. The compression and detection by the processor 94 converts the resultant signal 93 into corresponding image data 96, which is written into a memory 95. The memory 95 has line segments which correspond to scanning lines 71 respectively. The image data 96 is stored into the corresponding line segment of the memory 95. This process is reiterated for all scanning lines 71 so that image data 96 corresponding to one frame is stored in the memory 95. In FIG. 9, the data in the respective line segments of the memory 95 represent waveforms which occur in the case where the point A of FIG. 8 agrees with a reflection point.

Figure 10:
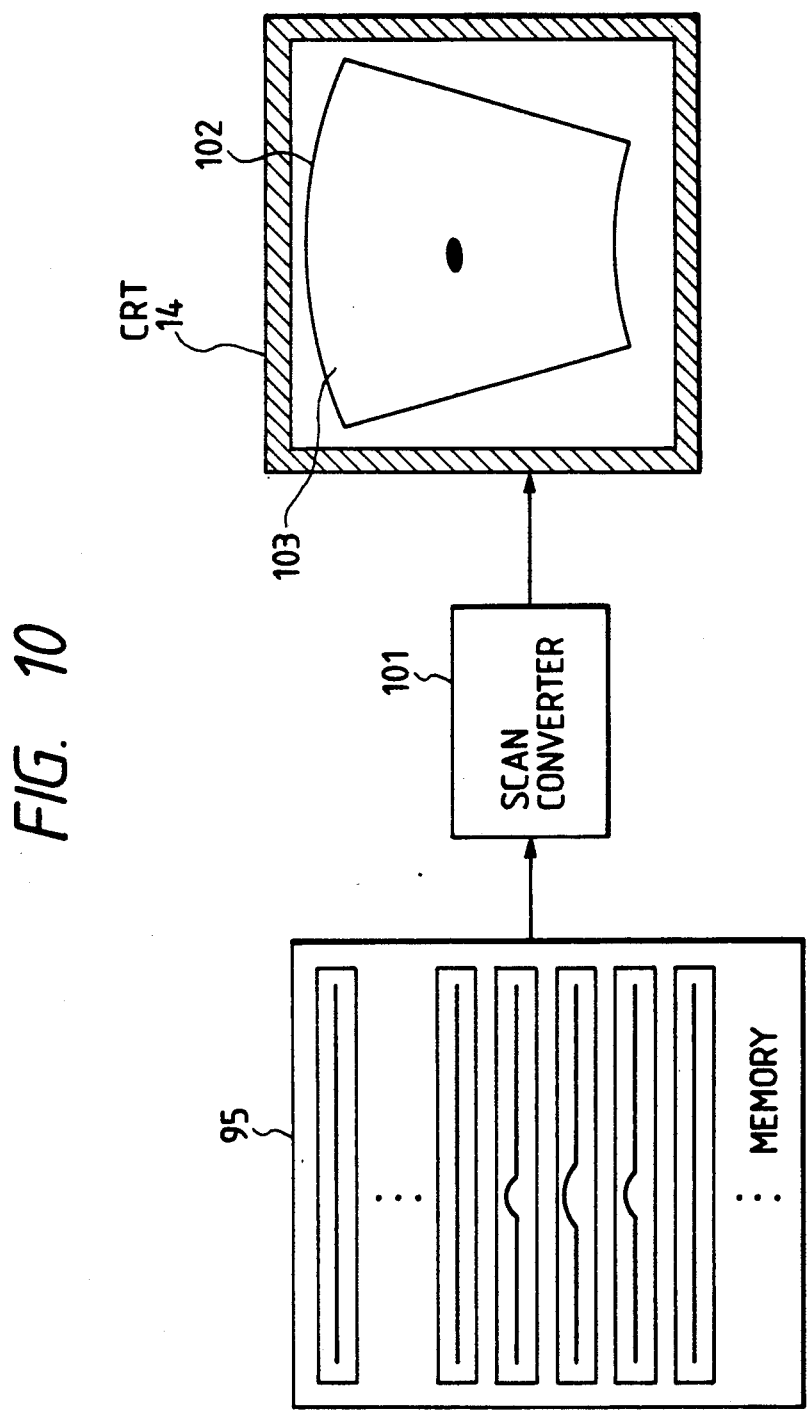
FIG. 10 is a block diagram of a signal processing part and an image displaying part of the ultrasonic diagnostic system according to the second embodiment of this invention.

With reference to FIG. 10, the image data are sequentially read out from the memory 95 by a digital scan converter 101, being converted by the scan converter 101 into a video signal. The video signal is fed to a CRT 14 so that an image 103 represented by the video signal is indicated on a sector region 102 of the CRT 14. The indicated image 103 agrees with an image of the sector scanned region 16 of the body. The indicated image 103 has a sector shape similar to the sector shape of the scanned region 16.

This embodiment features that the adverse effect of a grating lobe of the transducer element array 3 is suppressed by a weighting process considering a propagation path distribution.

DESCRIPTION OF THE THIRD PREFERRED EMBODIMENT

Figure 11:
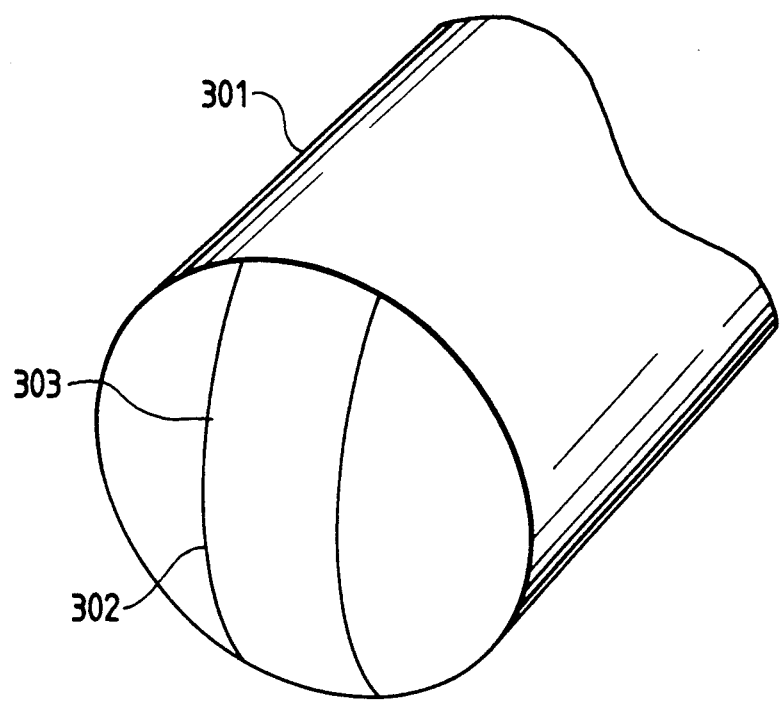
FIG. 11 is a perspective view of an ultrasonic probe in an ultrasonic diagnostic system according to a third embodiment of this invention.
Figure 12:
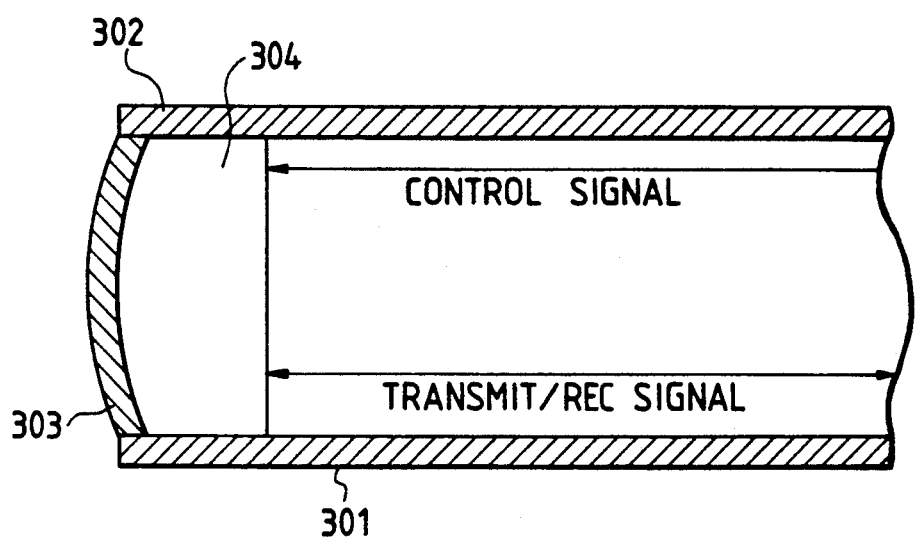
FIG. 12 is a sectional view of the ultrasonic probe of FIG. 11.

With reference to FIGS. 11 and 12, an ultrasonic diagnostic system includes an ultrasonic probe 301 provided on a front end of a catheter. The ultrasonic probe 301 has an ultrasonic wave transmitting/receiving section 302. The ultrasonic wave transmitting/receiving section 302 includes an array 303 of ultrasonic-to-electrical transducer elements, and an electronic circuit 304 associated with the transducer element array 303.

The transducer element array 303 has an ultrasonic wave transmitting/receiving surface which faces frontward with respect to the end of the catheter. The transducer element array 303 has a convex shape. The electronic circuit 304 is disposed in the region of the interior of the catheter which extends adjacently rearward of the transducer element array 303. The electronic circuit 304 is of a known structure, having a channel-changing function and a transmission/reception (T/S) switching function. During the transmission and the reception of ultrasonic wave via the transducer element array 303, the electronic circuit 304 selects one or more of the transducer elements as active elements and sequentially changes the active elements in a known manner. The electronic circuit 304 is electrically connected to a main part of the ultrasonic diagnostic system via signal lines. The signal lines extend in the interior of the catheter to conduct a transmission signal, a received signal, and a control signal to and from the electronic circuit 304.

Figure 13:
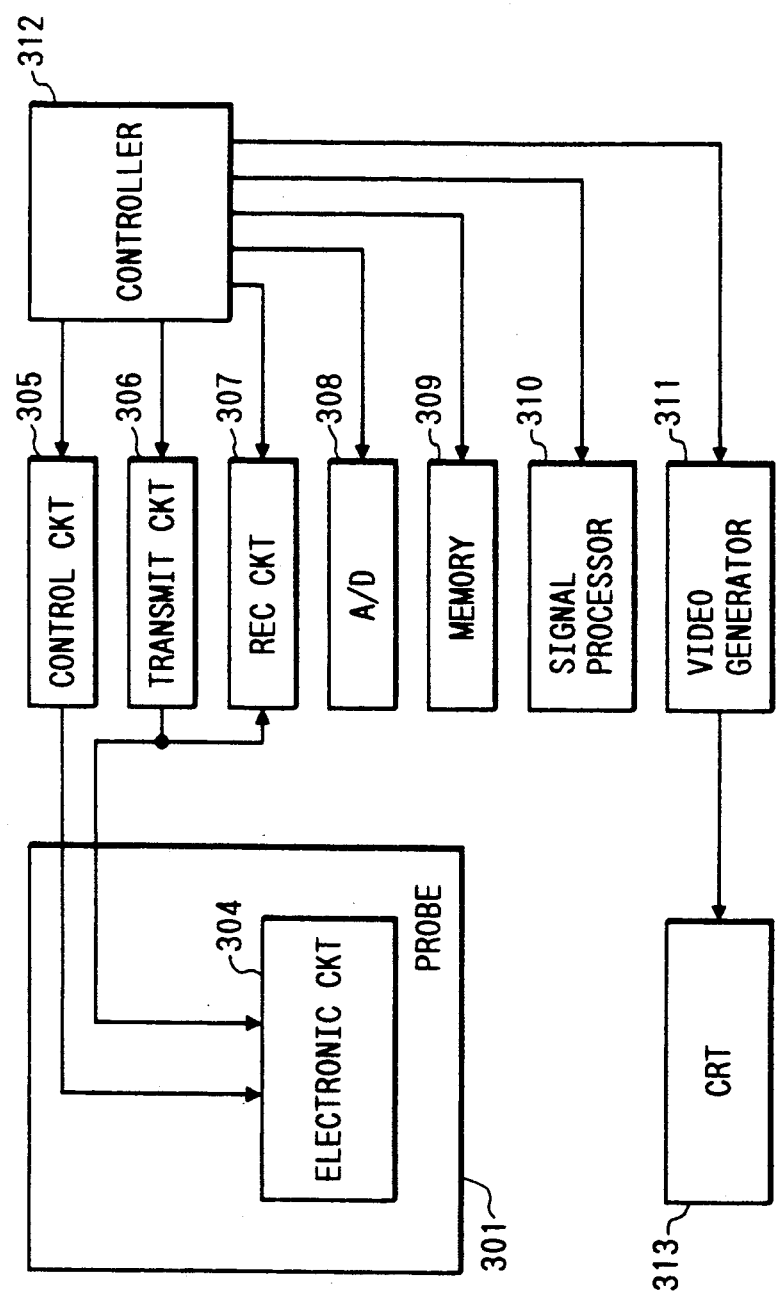
FIG. 13 is a block diagram of the ultrasonic diagnostic system according to the third embodiment of this invention.

As shown in FIG. 13, the main part of the ultrasonic diagnostic system includes a control circuit 305, a transmission circuit 306, and a reception circuit 307 connected to the electronic circuit 304 within the ultrasonic probe 301. The control circuit 305 serves to control the electronic circuit 304 in response to a signal fed from a controller 312. The transmission circuit 306 feeds a transmission signal to the transducer element array 303 via the electronic circuit 304 in response to a signal fed from the controller 312, and the transducer element array 303 emits ultrasonic wave in response to the transmission signal. Echoes of ultrasonic wave are received by the transducer element array 304 and are converted by the transducer element array 304 into corresponding electric signals, which are transmitted to the reception circuit 307 via the electronic circuit 304 and are amplified and processed by the reception circuit 307 in response to a signal fed from the controller 312.

The output signal from the reception circuit 307 is converted by an A/D converter 308 to a corresponding digital signal, which is stored into a memory 309. Timings of operation of the A/D converter 308 and the memory 309 are controlled by signals fed from the controller 312. The digital signal is read out from the memory 309, and is then processed by a signal processor 310 into image data in response to a signal fed from the controller 312. The image data is converted by a video generator 311 into a corresponding video signal in response to a signal fed from the controller 312. The video generator 311 includes a digital scan converter. The video signal is fed from the video generator 311 to a CRT 313, and an image represented by the video signal is indicated by the CRT 313. The devices 305-311 are controlled by the controller 312.

Figure 14:
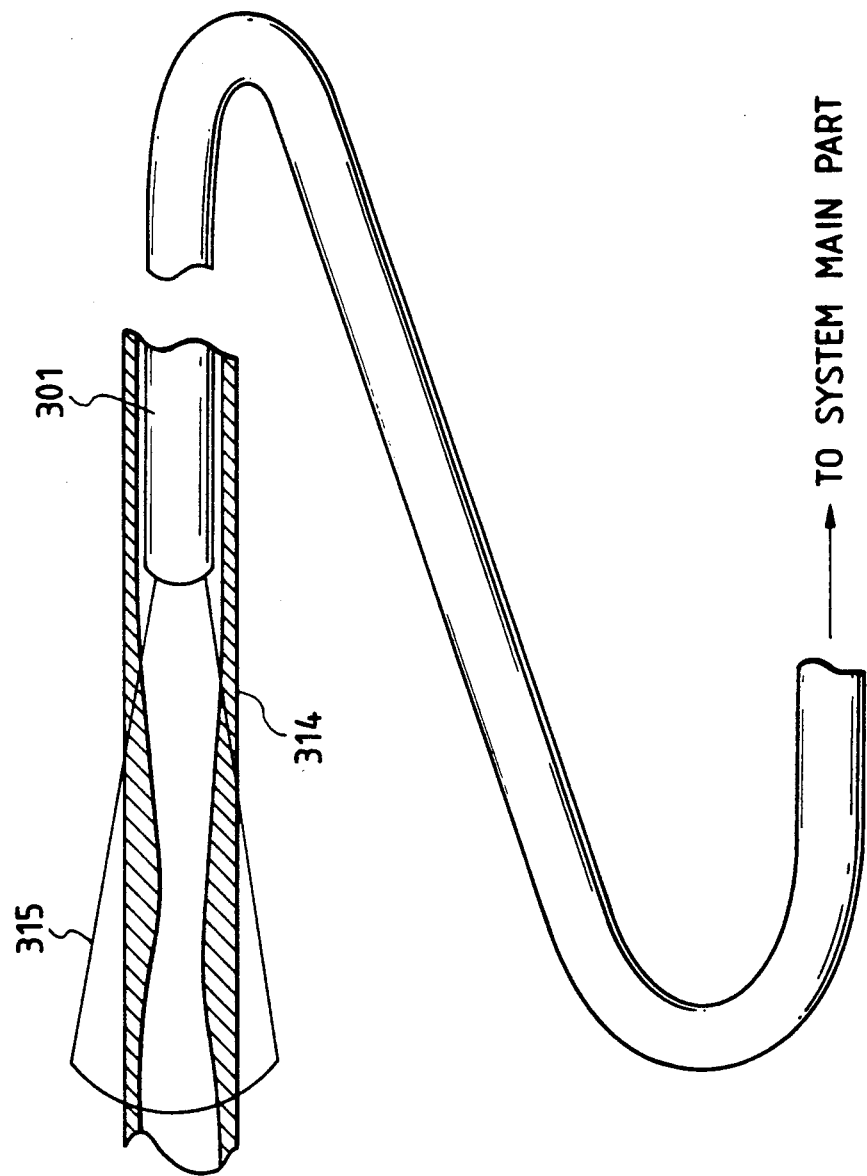
FIG. 14 is a sectional diagram showing a catheter in the ultrasonic diagnostic system according to the third embodiment of this invention.

The ultrasonic diagnostic system of FIGS. 11-13 operates as follows. As shown in FIG. 14, the catheter provided with the ultrasonic probe 301 is inserted into a blood vessel 314 of an examined body. One or more of the transducer elements in the transducer element array 303 are sequentially selected by the electronic circuit 304 as active transducer elements in response to a control signal fed from the control circuit 305. The selected transducer elements are fed with a transmission signal from the transmission circuit 306, emitting ultrasonic wave pulses toward a region of the body which extends in front of the end of the catheter.

Portions of the emitted ultrasonic wave pulses are reflected at blood vessel walls and other parts within the body, being returned to the transducer element array 303 as echo pulses. The echo pulses received by the selected transducer elements (the active transducer elements) are converted into corresponding electric echo signals, which are transmitted to the reception circuit 307 via the electronic circuit 304.

The transducer elements in the transducer element array 303 compose a given number of different channels. During the transmission and the reception of the ultrasonic wave pulses, the selected transducer elements are changed to sequentially activate the channels to scan a given sector region 315 of the body which extends in front of the catheter.

The echo signals are amplified and processed by the reception circuit 307. The output signal from the reception circuit 307 is converted by the A/D converter 308 into a corresponding digital signal, which is stored into the memory 309. The previously-mentioned process is reiterated and thus the digital signal is accumulated in the memory 309 until the digital signal in the memory 309 corresponds to a desired complete image of the body.

The signal processor 310 reads out the digital signal from the memory 309, subjecting the digital signal to a delaying process, a weighting process, and an adding process in accordance with an aperture synthesis technique and thereby converting the digital signal into image data. The image data is converted by the vedio generator 311 into a corresponding video signal. The video signal is fed from the video generator 311 to the CRT 313, and the image represented by the video signal is indicated by the CRT 313. The indicated image agrees with an image of the sector scanned region 315 of the body which extends in front of the end of the catheter. A sequence of the previously-mentioned operations is controlled by the controller 312. For this purpose, the controller 312 includes a time base.

The outside diameter of the ultrasonic probe 301 (the catheter) is preferably set to a small value, for example, 2 mm or less so that the ultrasonic probe 301 can be used within a small tube or coelom of the body. Since the ultrasonic probe 301 scans the region of the body which extends in front of the end of the catheter, a block of the tube or coelom of the body can be accurately observed.

Since the electronic circuit 304 is located adjacently rearward of the transducer element array 303, signal lines connected between the electronic circuit 304 and the transducer element array 303 are prevented from extending through a great part of the interior of the catheter. This is advantageous for the miniaturization of the catheter. When the electronic circuit 304 is composed of an IC chip, the ultrasonic probe 301 can be further miniaturized.

The frequency of the used ultrasonic wave is preferably set to a value within a range of 20 MHz to 40 MHz in consideration of the damping of the ultrasonic wave, the resolution of the obtained image, and the sizes of the ultrasonic probe 301 and the examined coelom and tube of the body. The transducer elements are preferably made of high-molecule piezoelectric material such as PVDF.

DESCRIPTION OF THE FOURTH PREFERRED EMBODIMENT

Figure 15:
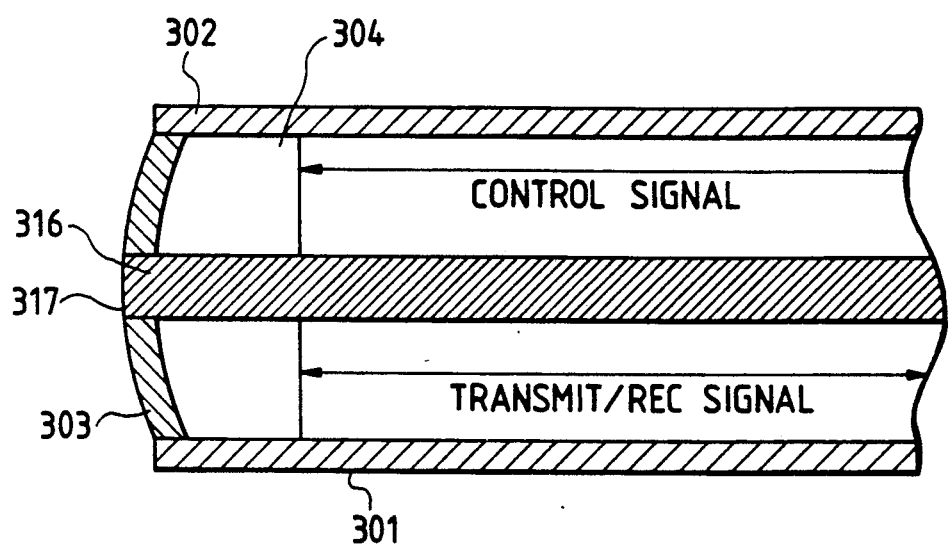
FIG. 15 is a sectional view of an ultrasonic probe in an ultrasonic diagnostic system according to a fourth embodiment of this invention.

FIG. 15 shows a fourth embodiment of this invention which is similar to the embodiment of FIGS. 11-14 except for an additional design indicated hereinafter.

As shown in FIG. 15, the fourth embodiment includes an optical fiber 316 extending along the central axis of a catheter. The optical fiber 316 is connected to a laser within a main part of an ultrasonic diagnostic system. The optical fiber 316 conducts a beam of light emitted from the laser. The optical fiber 316 extends through a transducer element array 303 and reaches the front end face of the catheter. The front end face of the catheter has an output window aperture 317 connected to the optical fiber 316. The laser light beam is emitted frontward from the end of the catheter via the output window aperture 317. The emitted laser light beam is used for treatment.

A wrong point in a tube or a blood vessel of an examined body can be treated by the application of the laser light beam while an image of a related part of the body is observed through ultrasonic imaging. To enable such a process, the output window aperture 317 and the transducer element array 303 are arranged so that the axis of the path of the emitted laser light beam will extend in the region scanned by the ultrasonic wave.

What is claimed is:

1. An ultrasonic diagnostic system comprising:
   a probe having an elongated catheter formed with an end face;
   an array of transducer elements disposed in the probe having a front side for emitting ultrasonic waves from the end face of the distal end of the probe and receiving echo ultrasonic waves, the transducer element array converting the received echo ultrasonic waves into corresponding electrical echo signals;
   processor means for processing the electrical echo signals to produce an image signal according to a predetermined aperture synthesis technique and for weighting the electrical echo signals to suppress components of the image signal which are caused by a grating lobe of the transducer element array, and for generating an image signal on the basis of the weighted electrical echo signals;
   display means for producing an image of a region in front of the end face of the probe in response to the image singal; and,
   means disposed in the distal end of the probe on the rear side of the transducer element array for sequentially activating the transducer elements during a respective transmission and reception process, and for sequentially transmitting the electric echo signals to the processor means.

2. The ultrasonic diagnostic system of claim 1 wherein the image region has a sector shape.

3. The ultrasonic diagnostic system of claim 1 further comprising means for scanning the region in front of the end face of the catheter according to a predetermined aperture synthesis technique.

4. The ultrasonic diagnostic system of claim 1 further comprising means for emitting a laser light beam from said catheter end face.

5. The ultrasonic diagnostic system of claim 4 wherein the emitting means comprises an optical fiber extending in the catheter and reaching an outlet window aperture in the end face of the catheter.

* * * * *